US006885890B2

(12) United States Patent
Spinelli et al.

(10) Patent No.: US 6,885,890 B2
(45) Date of Patent: Apr. 26, 2005

(54) APPARATUS AND METHOD FOR MULTI-SITE ANTI-TACHYCARDIA PACING

(75) Inventors: Julio C. Spinelli, Shoreview, MN (US); Qingsheng Zhu, Little Canada, MN (US); Andrew P. Kramer, Stillwater, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 438 days.

(21) Appl. No.: 10/027,794

(22) Filed: Dec. 20, 2001

(65) Prior Publication Data

US 2003/0120315 A1 Jun. 26, 2003

(51) Int. Cl.[7] .............................................. A61N 1/362
(52) U.S. Cl. ........................................................ 607/14
(58) Field of Search ................... 607/4, 9, 14

(56) References Cited

U.S. PATENT DOCUMENTS

| 4,830,006 A | 5/1989 | Haluska et al. ................. 607/4 |
| 5,002,052 A | 3/1991 | Haluska ........................ 607/4 |
| 5,107,850 A | 4/1992 | Olive .......................... 128/705 |
| 5,158,092 A | 10/1992 | Glace ......................... 600/518 |
| 5,161,529 A | 11/1992 | Stotts et al. ................. 128/419 |
| 5,181,511 A | 1/1993 | Nickolls et al. ...... 128/419 PG |
| 5,209,229 A | 5/1993 | Gilli ........................ 128/419 D |
| 5,222,493 A | 6/1993 | Sholder ................... 128/419 P |
| 5,224,475 A | 7/1993 | Berg et al. ............... 128/419 D |
| 5,251,624 A | 10/1993 | Bocek et al. .................. 607/6 |
| 5,324,310 A | 6/1994 | Greeninger et al. .......... 607/28 |
| 5,330,505 A | 7/1994 | Cohen .......................... 607/6 |
| 5,342,402 A | 8/1994 | Olson et al. ................... 607/5 |
| 5,350,410 A | 9/1994 | Kleks et al. |
| 5,379,776 A | 1/1995 | Murphy et al. ............. 128/705 |
| 5,425,749 A | 6/1995 | Adams ......................... 607/5 |

(Continued)

FOREIGN PATENT DOCUMENTS

| EP | 0709112 | 5/1996 | .......... A61N/1/365 |
| WO | WO-98/40122 | 9/1998 | ............ A61N/1/39 |

OTHER PUBLICATIONS

Mercando, et al., "Measurement of Differences in Timing and Sequence Between Two Ventricular Electrodes as a Means of Tachycardia Differentiation", *PACE, Part II*, vol. 9, (Nov.–Dec. 1986), 1069–1078.

*Primary Examiner*—George R. Evanisko
(74) *Attorney, Agent, or Firm*—Schwegman, Lundberg, Woessner & Kluth, P.A.

(57) ABSTRACT

An apparatus and method for treating ventricular tachycardia in which paces are delivered to the ventricles at multiple pacing sites in accordance with an anti-tachycardia pacing protocol. Paces are delivered at a selected offset interval in a manner that both resynchronizes ventricular contractions and increases the probability of terminating the tachycardia.

18 Claims, 3 Drawing Sheets

U.S. PATENT DOCUMENTS

| | | | |
|---|---|---|---|
| 5,472,453 A | 12/1995 | Alt | 607/4 |
| 5,548,619 A | 8/1996 | Horiike et al. | 375/344 |
| 5,587,970 A | 12/1996 | Greenwood | 368/10 |
| 5,662,688 A | 9/1997 | Haefner et al. | 607/5 |
| 5,683,424 A | 11/1997 | Brown et al. | 607/5 |
| 5,683,431 A | 11/1997 | Wang | 607/28 |
| 5,755,737 A | 5/1998 | Prieve et al. | 607/4 |
| 5,836,971 A | 11/1998 | Starkweather | 607/4 |
| 5,846,263 A | 12/1998 | Peterson et al. | 607/14 |
| 5,855,593 A | 1/1999 | Olson et al. | 607/9 |
| 5,871,512 A | 2/1999 | Hemming et al. | 607/28 |
| 5,978,707 A | 11/1999 | Krig et al. | 607/14 |
| 5,999,854 A | 12/1999 | Deno et al. | 607/18 |
| 6,101,414 A | 8/2000 | Kroll | 607/14 |
| 6,128,529 A | 10/2000 | Elser | 607/4 |
| 6,137,308 A | 10/2000 | Nayak | 326/39 |
| 6,151,524 A | 11/2000 | Krig et al. | 607/14 |
| 6,167,308 A | 12/2000 | DeGroot | |
| 6,192,275 B1 | 2/2001 | Zhu et al. | 607/28 |
| 6,289,248 B1 | 9/2001 | Conley et al. | 607/59 |
| 6,400,986 B1 | 6/2002 | Sun et al. | 607/14 |
| 6,477,422 B1 | 11/2002 | Splett | 607/28 |
| 6,654,639 B1 * | 11/2003 | Lu | 607/14 |
| 2002/0058968 A1 | 5/2002 | Sun et al. | 607/14 |
| 2003/0083703 A1 | 5/2003 | Zhu et al. | 607/14 |

* cited by examiner

APPARATUS AND METHOD FOR MULTI-SITE ANTI-TACHYCARDIA PACING

FIELD OF THE INVENTION

This invention pertains to systems and methods for treating arrhythmias with electrical stimulation.

BACKGROUND

Cardiac rhythm management devices are implantable devices that provide electrical stimulation to selected chambers of the heart in order to treat disorders of cardiac rhythm and include pacemakers and implantable cardioverter/defibrillators (ICD's). A pacemaker is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Pacing therapy may also be applied in order to treat cardiac rhythms that are too fast, termed anti-tachycardia pacing. (As the term is used herein, a pacemaker is any cardiac rhythm management device with a pacing functionality, regardless of any other functions it may perform such as the delivery cardioversion or defibrillation shocks to terminate atrial or ventricular fibrillation.)

Also included within the concept of cardiac rhythm is the manner and degree to which the heart chambers contract during a cardiac cycle to result in the efficient pumping of blood. For example, the heart pumps more effectively when the chambers contract in a coordinated manner. The heart has specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways, such as bundle branch blocks, can thus suffer compromised cardiac output.

Heart failure refers to a clinical syndrome in which an abnormality of cardiac function causes a below normal cardiac output that can fall below a level adequate to meet the metabolic demand of peripheral tissues. It usually presents as congestive heart failure (CHF) due to the accompanying venous and pulmonary congestion. Heart failure can be due to a variety of etiologies with ischemic heart disease being the most common. Some heart failure patients suffer from some degree of AV block or are chronotropically deficient such that their cardiac output can be improved with conventional bradycardia pacing. Such pacing, however, may result in some degree of uncoordination in atrial and/or ventricular contractions because pacing excitation from a single pacing site is spread throughout the myocardium only via the much slower conducting muscle fibers of either the atria or the ventricles, and not the specialized conduction pathways. Most pacemaker patients can still maintain more than adequate cardiac output with artificial pacing, but the diminishment in cardiac output may be significant in a heart failure patient whose cardiac output is already compromised. Intraventricular and/or interventricular conduction defects are also commonly found in heart failure patients and can contribute to cardiac dysfunction by causing unsynchronized contractions during intrinsic beats. In order to treat these problems, cardiac rhythm management devices have been developed which provide electrical pacing stimulation to one or more heart chambers in an attempt to improve the coordination of atrial and/or ventricular contractions, termed cardiac resynchronization therapy.

One form of cardiac resynchronization therapy is biventricular pacing in which paces are delivered to each ventricle during a paced cardiac cycle separated by a specified resynchronization offset interval. The paces may be delivered in accordance with a bradycardia pacing mode in order to both resynchronize the ventricles and maintain an adequate heart rate. Patients treated in this manner may also occasionally suffer from ventricular tachyarrhythmias such as ventricular tachycardia. The implanted pacemaker may therefore also be programmed to deliver anti-tachycardia pacing therapy when a ventricular tachycardia is detected. Conventional anti-tachycardia pacing, however, involves pacing at only a single site of one ventricle, and the beneficial effects of resynchronization therapy upon cardiac output are lost while the anti-tachycardia pacing therapy is being delivered. The resulting diminishment in cardiac output may also lessen blood flow to the myocardium and increase the chances that the ventricular tachycardia degenerates into fibrillation.

SUMMARY OF THE INVENTION

The present invention is an apparatus and method for delivering anti-tachycardia pacing therapy in appropriately selected patients that more efficiently terminates a ventricular tachycardia. In addition, in certain patients it also improves hemodynamics during the pacing by resynchronizing the ventricles. For anti-tachycardia pacing to be effective, the delivered paces must induce a propagating depolarization (i.e., achieve capture) that counteracts the tachycardia. In order to increase the probability of capturing the ventricle during a ventricular tachycardia, the initial pace of a multi-site anti-tachycardia pacing sequence is delivered to a primary ATP site at a specified coupling interval after detection of a sense at that site. The primary ATP site is preferably that site among the available pacing sites that depolarizes earliest during the ventricular tachycardia. One or more other pacing sites, designated secondary ATP sites, each receive a pace delivered at an ATP ventricular offset interval selected to be approximately equal to the conduction time for a depolarization originating at the primary ATP site to reach the secondary ATP site. In this manner, the probability that the pace to the secondary ATP site also achieves capture is increased. The value of the ATP ventricular offset interval may be selected by measuring a conduction time for a depolarization to reach a secondary ATP site.

In one embodiment of the invention, a cardiac rhythm management device is configured to deliver ventricular resynchronization therapy via biventricular pacing so that a pace is delivered to each ventricle. These resynchronization paces may be separated by a programmed resynchronization offset interval. Upon detection of a ventricular tachycardia, the device is operated so as to pace a primary ATP ventricle (i.e., either the right or left ventricle) with an anti-tachycardia pacing sequence in accordance with a selected anti-tachycardia pacing (ATP) protocol. Such an anti-tachycardia pacing sequence may be a train of multiple paces or consist of only one pace. A pace is also delivered to the contralateral secondary ATP ventricle at a selected ATP offset interval after each pace delivered to the primary ATP ventricle in the anti-tachycardia pacing sequence. The primary ATP ventricle is selected as the ventricle from which a sense is detected earliest during a cycle of the ventricular tachycardia. The ATP offset is selected to be the delay between intrinsic depolarizations of the primary and secondary ATP ventricles measured during the ventricular tachycardia that, in general, may not be equal to the resynchronization offset interval. If the ventricular tachycardia is unstable, the ATP offset interval may be selected to less than the minimum measured delay. After capture is achieved and the ventricular tachycardia is terminated, the offset interval reverts back to the programmed resynchronization offset interval.

The above summary is intended to provide an overview of the subject matter of the present patent application. It is not intended to provide an exhaustive or exclusive explanation of the invention.

DETAILED DESCRIPTION

Figure 1:
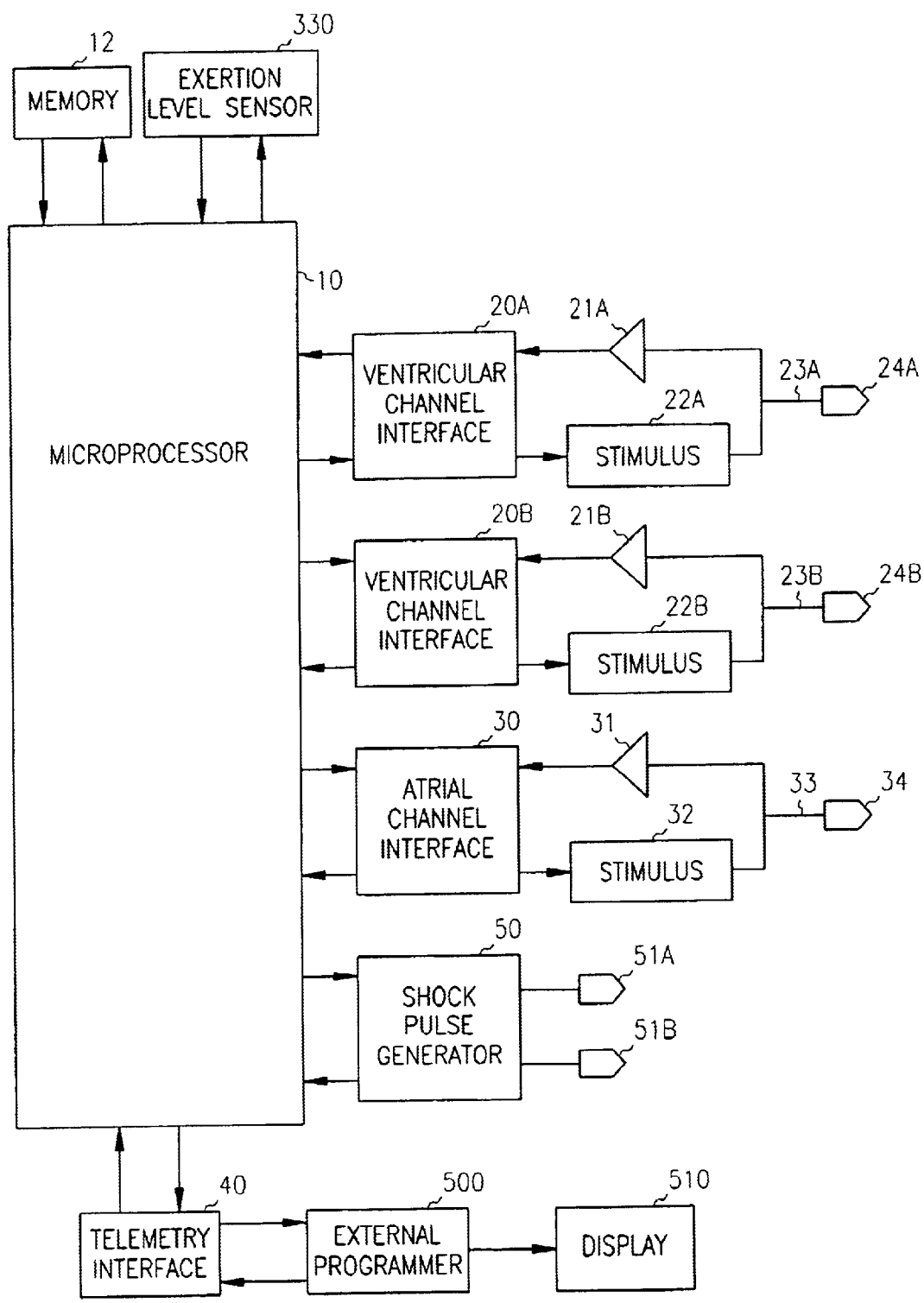
FIG. 1 is a system diagram of a cardiac rhythm management device.

Pacemakers are typically implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. An electrogram signal sensed by an electrode corresponding to a depolarization wave associated with an intrinsic contraction of the atria or ventricles that exceeds a predetermined threshold is referred to as an atrial sense or ventricular sense, respectively. In order to cause a contraction in the absence of an intrinsic beat, a pacing pulse (either an atrial pace or a ventricular pace) with energy above a certain pacing threshold is delivered to the chamber.

As aforesaid, the present invention relates to the delivery of ATP therapy via multiple pacing sites. After a description of basic pacing modes and an exemplary pacemaker, a detailed description is given.

1. Pacing Modes

Bradycardia pacing modes refer to pacing algorithms used to pace the atria and/or ventricles when the intrinsic ventricular rate is inadequate either due to AV conduction blocks or sinus node dysfunction. Such modes may either be single-chamber pacing, where either an atrium or a ventricle is paced, or dual-chamber pacing in which both an atrium and a ventricle are paced. Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker.

Cardiac resynchronization therapy is pacing stimulation applied to one or more heart chambers in a manner that restores or maintains synchronized bilateral contractions of the atria and/or ventricles and thereby improves pumping efficiency. It is advantageous to deliver resynchronization therapy in conjunction with one or more synchronous bradycardia pacing modes. Resynchronization therapy may then be implemented by pacing one site, designated as the rate site, with a bradycardia pacing mode and adding synchronized pacing by pacing one or more synchronized pacing sites in a defined time relation to one or more selected sensing and pacing events that either reset escape intervals or trigger paces in the bradycardia pacing mode. One synchronized pacing mode may be termed offset synchronized pacing. In this mode, one or more synchronized sites are paced with a positive, negative, or zero timing offset, referred to as the resynchronization offset interval, as measured from a pace delivered to the rate site or a sense at that site. The offset interval may be zero in order to pace the sites simultaneously, positive in order to pace the synchronized sites after the rate site, or negative to pace the synchronized site before the primary site. One example of such pacing is biventricular offset pacing where both ventricles are paced with a specified resynchronization offset interval. A first ventricle (i.e., either the right or left) is designated as the rate ventricle and paced with an escape interval that is reset by either a sensed depolarization or a pace in that ventricle. The contralateral synchronized ventricle is then paced at resynchronization offset interval with respect to either a sense or a pace in the rate ventricle. The value of the resynchronization offset interval would normally be individually specified to optimize cardiac output, given the conduction problems in a particular patient.

Another pacing mode is anti-tachycardia pacing (ATP). In ATP, the heart is competitively paced with one or more pacing pulses in an effort to interrupt reentrant circuits causing the tachycardia. Modem ICD's typically have ATP capability so that ATP therapy is delivered to the heart when a tachycardia is detected, while a shock pulse is delivered when fibrillation occurs. Although cardioversion/defibrillation will terminate tachycardia, it consumes a large amount of stored power from the battery and results in patient discomfort owing to the high voltage of the shock pulses. It is desirable, therefore, for the ICD to use ATP to terminate a tachyarrhythmia whenever possible. Generally, only cardioversion/defibrillation will terminate fibrillation and certain high rate tachycardias, while ATP can be used to treat lower rate tachycardias.

In most ICD's with ATP capability, ventricular fibrillation (VF) is distinguished from ventricular tachycardia (VT) using rate-based criteria so that ATP or shock therapy can be delivered as appropriate. The heart rate is usually measured by detection of the time between successive R waves (i.e., ventricular depolarizations). A measured heart rate is classified as a tachycardia when the rate is in a VT zone, defined as a range of rates above a tachycardia detection rate (TDR) but below a fibrillation detection rate (FDR). A measured heart rate above the FDR, on the other hand, is in the VF zone and is classified as a fibrillation. In a typical device, a tachycardia with a heart rate in the VT zone is treated with ATP therapy in order to avoid an unnecessary painful shock to the patient, and a defibrillation shock is delivered if the pacing fails to terminate the arrhythmia.

2. System Description

FIG. 1 shows a system diagram of a microprocessor-based pacemaker physically configured with sensing and pacing channels for both atria and both ventricles. The controller 10 of the pacemaker is a microprocessor that communicates with a memory 12 via a bidirectional data bus. The memory 12 typically comprises a ROM (read-only memory) for program storage and a RAM (random-access memory) for data storage. The controller 10 controls the overall operation of the device in accordance with programmed instructions stored in memory, including controlling the delivery of paces via the pacing channels, interpreting sense signals from the sensing channels, and implementing timers for defining escape intervals and sensory refractory periods. Both bradycardia and anti-tachycardia pacing modes may be implemented in code executed by the controller.

The pacemaker has an atrial sensing and pacing channel comprising electrode 34, lead 33, sensing amplifier 31, pulse generator 32, and atrial channel interface 30 that communicate bidirectionally with microprocessor 10. The device also has ventricular sensing and pacing channels for both ventricles comprising electrodes 24*a–b*, leads 23*a–b*, sensing amplifiers 21*a–b*, pulse generators 22*a–b*, and ventricular channel interfaces 20*a–b*. In the figure, "a" designates one ventricular channel and "b" designates the channel for the contralateral chamber. In this embodiment, a single electrode is used for sensing and pacing in each channel, known as a unipolar lead. Other embodiments may employ bipolar leads that include two electrodes for outputting a pacing pulse and/or sensing intrinsic activity. The channel interfaces 20*a–b* and 30 include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. An exertion level sensor 330 (e.g., an accelerometer or a minute ventilation sensor) enables the controller to adapt the pacing rate in accordance with changes in the patient's physical activity. A telemetry interface 40 is also provided for communicating with an external programmer 500 that has an associated display 510.

In addition to bradycardia and resynchronization pacing, the sensing and pacing channels can be used for anti-tachycardia pacing and for measuring heart rate in order to detect tachycardia and fibrillation. The controller 10 analyzes the signals received from the sensing channels to detect and type arrhythmias and controls the operation of the pacing channels in order to deliver ATP therapy in accordance with a selected protocol. A shock pulse generator 50 is also interfaced to the microprocessor for delivering cardioversion or defibrillation pulses to the heart via a pair of electrodes 51*a* and 51*b*. The device delivers ATP therapy or a defibrillation shock under programmed control of the microprocessor in response to sensed activity from the sensing channels. A sensing routine analyzes the electrical activity received from the sensing channels in order to detect an arrhythmia, and the arrhythmia is then classified as a tachycardia (i.e., a terminable arrhythmia) or fibrillation based upon rate.

3. Multi-site Anti-tachycardia Pacing

Pacing protocols for ATP therapy involve delivering a sequence of one or more pulses in timed relation to detected intrinsic depolarizations during an episode of tachycardia, the timed relation referred to as a coupling interval. The objective of anti-tachycardia pacing is to block the reentrant depolarization wavefront causing the tachycardia with competitive pacing pulses. ATP protocols vary according to parameters that define the number of pulses delivered and the particular timing employed. Whether the sequence consists of only one pulse or a train of pulses with constant or variable inter-pulse delays, in order to be effective, the pacing pulse or pulses must induce a propagating depolarization wavefront in the myocardium, referred to as capture. Achieving capture requires that the pacing pulse be delivered when the myocardium is in a non-refractory state. This is complicated by the fact that, during a ventricular tachycardia, the action potential takes up a large portion of the total cycle length, leaving only a small window during which the myocardium is non-refractory. Accordingly, a coupling interval should be specified so that the ATP pacing pulse, or initial pulse of a multiple pulse sequence, is delivered within this window. The ATP pacing sequence is then able to capture the ventricle and induce a propagating wavefront that terminates the tachycardia.

In patients treated with ventricular resynchronization therapy, however, achieving sufficient capture of the ventricular myocardium in a manner that terminates a ventricular tachycardia is complicated by the pathological conduction velocities within or between the ventricles. For example, an ATP pacing pulse may capture the ventricle receiving the pace but not the contralateral ventricle owing to an abnormal interventricular conduction delay. It would be desirable to deliver multi-site pacing that achieves simultaneous capture of the ventricular myocardium at the pacing sites used for resynchronization pacing. The existing ventricular conduction delays, however, may make it impossible or very unlikely to find a single coupling interval for delivering a multi-site ATP sequence that is able to do so. Anti-tachycardia pacing could be delivered with a pace to each ventricle using the same resynchronization offset interval as specified for the biventricular resynchronization pacing. That is, first and second paces would be delivered to first and second ventricles (e.g., right and left ventricles) separated by the resynchronization offset interval for each pace of the anti-tachycardia pacing sequence, with the first pace of a sequence delivered to the first ventricle after a specified coupling interval with respect to a sense in the first ventricle. The problem with delivering biventricular anti-tachycardia pacing with the specified resynchronization offset interval is that the pace to the second ventricle may not be delivered after an appropriate coupling interval with respect to an intrinsic depolarization in that ventricle and thus may not achieve capture. The spatial electrical inhomogeneity created by the abnormally long ventricular conduction times may then not be eliminated by the ATP therapy. Since biventricular anti-tachycardia pacing involves interspersing pairs of paces to the ventricles with intrinsic beats with the goal of capturing the ventricles with the pacing pulses, the lack of capture by the pace to the second ventricle also means that no resynchronization is being obtained by the paces.

Figure 2:
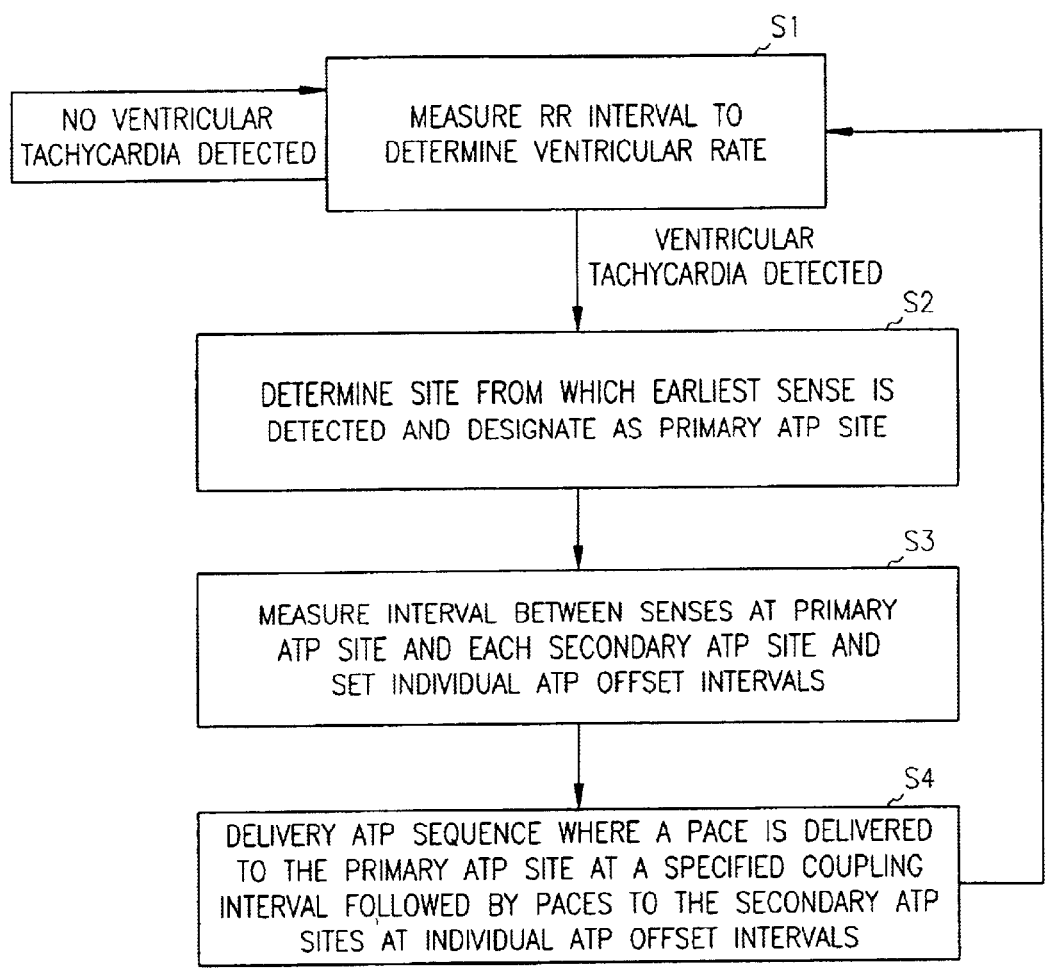
FIG. 2 illustrates an exemplary implementation.

In accordance with the invention, a ventricular tachycardia is treated by delivering ATP therapy to the ventricles at multiple pacing sites. FIG. 2 illustrates an exemplary implementation as would be performed by the controller of a cardiac rhythm management device equipped with appropriate multiple sensing and pacing channels. It is recognized that the multiple pacing sites used for ATP may be the same as those used for delivering ventricular resynchronization therapy. At step S1, the ventricular rate is monitored, concurrent with the delivery of any other kind of pacing therapy that may be programmed into the device. When a ventricular tachycardia is detected, the device determines at step S2 from which of the multiple sensing/pacing sites the earliest sense is detected during the tachycardia, that site being designated the primary ATP site and the other pacing sites designated as secondary ATP sites. At step S3, the intervals between a sense at the primary ATP site and each secondary ATP site during the tachycardia is measured. At step S4, an ATP sequence is delivered, where the primary ATP site receives a pace at a specified coupling interval with respect to a sense at that site. The secondary ATP pacing sites then receive paces at individual ATP offset intervals with respect to the pace delivered to the primary ATP site. For each secondary ATP site, the ATP offset interval is selected to equal the measured time interval between a senses at the secondary site and the primary site at determined at step S3. The ATP offset intervals thus approximate the difference between the depolarization times of the primary ATP site and the secondary ATP sites. In one embodiment, a biventricular ATP sequence is delivered such that paces are delivered to a primary ATP ventricle and the contralateral secondary ATP ventricle separated by a specified ATP offset interval instead of the specified resynchronization offset interval used for biventricular resynchronization pacing. The primary ATP ventricle is selected as the ventricle that contracts first during the ventricular tachycardia (i.e., the ventricle from which a sense is detected earliest during a cycle of the ventricular tachycardia), and the ATP offset interval is selected to correspond to the time delay between depolarizations of the primary and secondary ATP ventricles (i.e., the measured time interval between senses detected from the primary and secondary ATP ventricles during a single cycle). When the delay between the depolarizations is variable, as is the case in certain unstable ventricular tachycardias, the ATP offset interval may be selected to be less than or equal to a minimum measured delay value.

Figure 3A:
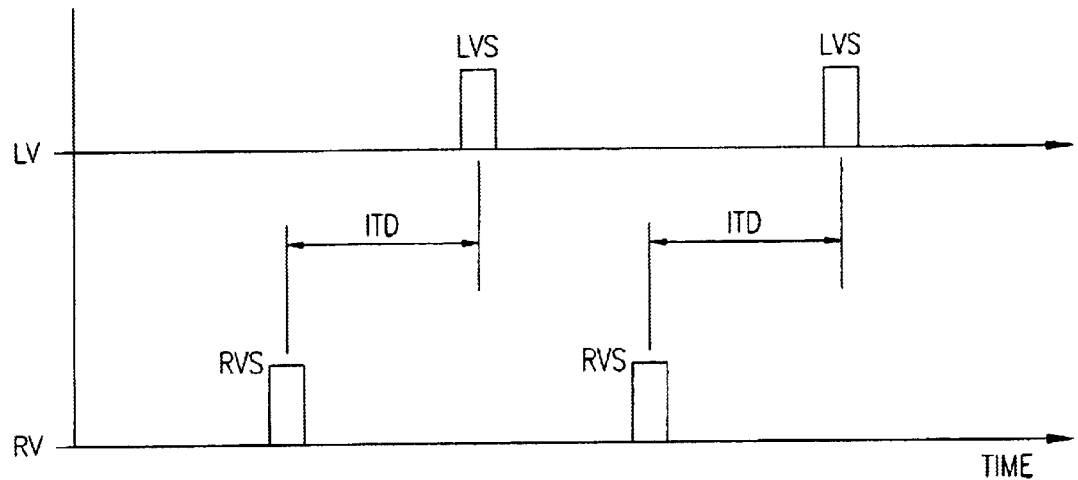
FIGS. 3A and 3B are timing diagrams illustrating the operation of the ATP ventricular offset interval.
Figure 3B:
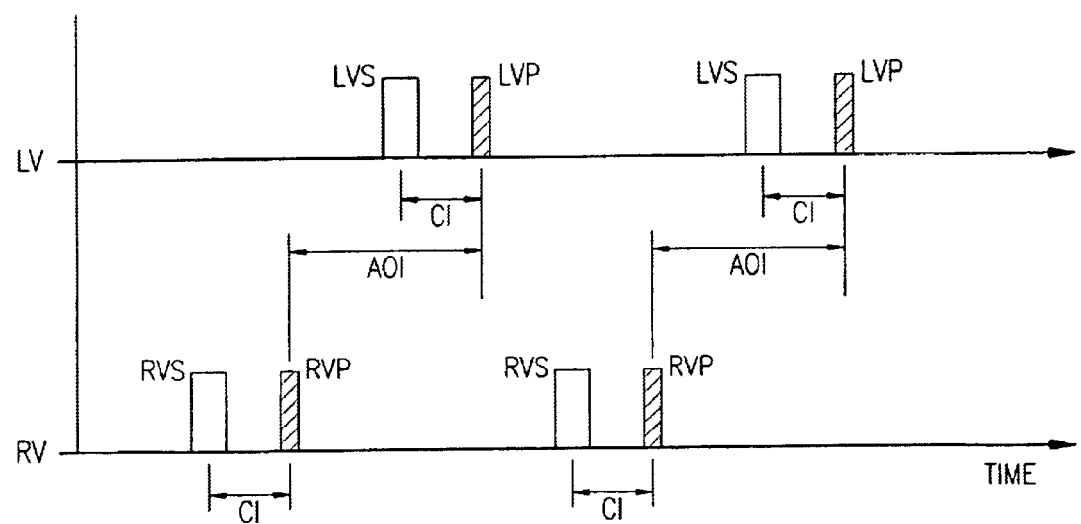

FIG. 3A is a timeline of the right ventricular sensing channel RV and left ventricular sensing channel LV, where the primary and secondary ATP ventricles are the right and left ventricles, respectively. The diagram illustrates the intrinsic time delay ITD existing between sensed depolarizations RVS and LVS of the right and left ventricles, respectively, when ventricular tachycardia originating in the right ventricle is present. FIG. 3B shows ATP pacing pulse pairs delivered at a specified coupling interval CI with respect to a right ventricular sense RVS during an episode of ventricular tachycardia. The paces are separated by an ATP offset interval AOI. If the ATP offset interval AOI is made to correspond to the intrinsic time delay ITD, both paces are delivered to their respective ventricles at the coupling interval CI. Thus, by delivering the pair of paces to the ventricles after an appropriately specified coupling interval with respect to a sensed intrinsic depolarization in the primary ATP ventricle, both paces have an increased chance of occurring within a non-refractory window and achieving capture. This increases the likelihood that the tachycardia will be terminated by inducing a propagating wavefront in each ventricle and delivers some resynchronization to the ventricles, albeit not in an optimum manner.

The controller of an implanted cardiac rhythm management device such as that illustrated in FIG. 1 may be programmed to implement the invention with biventricular ATP as follows. The separate ventricular sensing channels are used to detect senses in the right and left ventricles, and a ventricular tachycardia is then detected when a time interval between successive depolarizations in one of the ventricles meets a specified rate criterion. Upon detection of a ventricular tachycardia, the ventricle that depolarizes first is designated as the primary ATP ventricle with the contralateral ventricle designated as the secondary ATP ventricle. An anti-tachycardia pacing sequence is then delivered in accordance with a selected anti-tachycardia pacing (ATP) protocol, with the sequence being delivered at a selected coupling interval with respect to detection of an intrinsic depolarization in the primary ATP ventricle. With each pace of the anti-tachycardia pacing sequence delivered to the primary ATP ventricle, a pace is also delivered to the secondary ATP ventricle at a selected ATP ventricular offset interval. The anti-tachycardia pacing sequence is thus made up of a single pair of paces or multiple pairs of paces delivered to each ventricle. The ATP ventricular offset interval is set to approximately equal the time delay between a depolarization sensed first at the primary ATP ventricle and sensed subsequently at the secondary ATP ventricle. The implanted device may measure this intrinsic time delay using the sensing channels when intrinsic beats occur, or the time delay may be measured by other means and programmed into the implanted device. In certain embodiments, the intrinsic time delay is an average of a plurality of measured intervals between ventricular depolarizations occurring in the primary and secondary ATP ventricles during a ventricular tachycardia. In this manner, a pace is delivered to each of the two ventricles approximately at the specified coupling interval with respect to an intrinsic depolarization occurring in the ventricle.

After the ATP sequence achieves capture and the episode of ventricular tachycardia is terminated, the device may revert to a normal ventricular resynchronization pacing mode with specified resynchronization offset intervals and designated rate and synchronized pacing sites. In a multi-site pacing configuration with only two ventricular pacing sites, the offset between the ventricular paces may be abruptly or gradually returned from the ATP offset interval to the resynchronization offset interval. Preferably, the offset interval is reverted smoothly, at no more than 10 milliseconds per beat, to the normal programmed resynchronization offset interval.

Although the invention has been described in conjunction with the foregoing specific embodiment, many alternatives, variations, and modifications will be apparent to those of ordinary skill in the art upon reading and understanding the present description. Such alternatives, variations, and modifications are intended to fall within the scope of the following appended claims.

What is claimed is:

1. A method for operating a cardiac rhythm management device, comprising:

detecting senses from multiple ventricular sites, where a sense corresponds to an intrinsic depolarization occurring at the site;

detecting a ventricular tachycardia when a time interval between successive senses detected from one of the sites meets a specified rate criterion;

pacing one of the sites designated as the primary anti-tachycardia pacing (ATP) site with an anti-tachycardia pacing sequence in accordance with an ATP protocol when a ventricular tachycardia is detected, wherein the sequence is delivered at a selected coupling interval with respect to detection of a sense at the primary ATP site;

pacing one or more of the other sites, designated as secondary ATP sites, at a selected ATP offset interval with respect to a pace delivered to the primary ATP site in the anti-tachycardia pacing sequence; and, reverting to a ventricular resynchronization paging mode when the ventricular tachycardia is terminated, wherein in the resynchronization mode one of the sites is designated as the rate site and paced with a bradycardia pacing mode and one or more of the other sites are paced at specified resynchronization offset intervals with respect to paces delivered to the rate site.

2. The method of claim 1 wherein the primary ATP site is selected as the site from which a sense is detected earliest during a single cycle of the ventricular tachycardia.

3. The method of claim 1 wherein the ATP offset interval for a particular secondary ATP site is selected to be approximately equal to a measured time delay between a sense detected from the primary ATP site and a sense detected at the particular ATP site.

4. The method of claim 1 wherein the ATP offset interval for a particular secondary ATP site is selected to be less than or equal to a minimum measured time delay between a sense detected from the primary ATP site and a sense detected at the particular ATP site.

5. The method of claim 1 wherein a single site is located in each ventricle such that biventricular ATP therapy is delivered upon detection of a ventricular tachycardia with one of the ventricles designated as the primary ATP ventricle and the contralateral ventricle is designated as the secondary ATP ventricle, and further wherein an anti-tachycardia pacing sequence in accordance with a selected anti-tachycardia pacing (ATP) protocol is delivered to the primary ATP ventricle at a selected coupling interval with respect to detection of a sense in the primary ATP ventricle, and further wherein the secondary ATP ventricle is paced at a selected ATP offset interval with respect to the pace delivered to the primary ATP ventricle in the anti-tachycardia pacing sequence.

6. The method of claim 5 further comprising reverting to a biventricular resynchronization pacing mode upon termination of the ventricular tachycardia.

7. The method of claim 6 wherein the offset interval between paces to the ventricles gradually changes from the ATP offset interval to a programmed resynchronization offset interval upon termination of the ventricular tachycardia.

8. The method of claim 5 wherein the primary ATP ventricle is selected as the ventricle from which the earliest sense is detected during a cycle of the ventricular tachycardia.

9. The method of claim 5 wherein the ATP offset interval is selected to be approximately equal to a measured time delay between a sense in the primary ATP ventricle and a sense in the secondary ATP ventricle during a cycle of the ventricular tachycardia.

10. A cardiac rhythm management device, comprising:
sensing channels for detecting senses from multiple ventricular sites, where a sense corresponds to an intrinsic depolarization occurring at the site;
pacing channels for delivering paces to the multiple ventricular sites;
a controller for controlling the delivery of paces in accordance with a programmed pacing mode; and,
wherein the controller is programmed to;
detect a ventricular tachycardia when a time interval between successive senses at a site meets a specified rate criterion;

pace one of the sites designated as the primary ATP site with an anti-tachycardia pacing sequence in accordance with an anti-tachycardia pacing protocol when a ventricular tachycardia is detected, wherein the sequence is delivered at a selected coupling interval with respect to detection of a sense at the primary ATP site;

pace one or more of the other sites, designated as secondary ATP sites, at a selected ATP offset interval with respect to a pace delivered to the primary ATP site in the anti-tachycardia pacing sequence; and, revert to a ventricular resynchronization pacing mode when the ventricular tachycardia is terminated, wherein in the resynchronization mode one of the sites is designated as the rate site and paced with a bradycardia pacing mode and one more of the other sites are paced at specified resynchronization offset intervals with respect to paces delivered to the rate site.

11. The device of claim 10 wherein the controller is programmed to select the primary ATP site as the site from which a sense is detected earliest during a single cycle of the ventricular tachycardia.

12. The device of claim 10 wherein the controller is programmed t select the ATP offset interval for a particular secondary ATP site to be approximately equal to measured time delay between a sense detected from the primary ATP site and a sense detected at the particular ATP site.

13. The device of claim 10 wherein the controller is programmed to select the ATP offset interval for a particular secondary ATP site to be less than or equal to a minimum measured time delay between a sense detected from the primary ATP site and a sense detected at the particular ATP site.

14. The device of claim 10 wherein a single site is located in each ventricle such that biventricular ATP therapy is delivered upon detection of a ventricular tachycardia with one of the ventricles designated as the primary ATP ventricle and the contralateral ventricle is designated as the secondary ATP ventricle, and further wherein the controller is programmed such that an anti-tachycardia pacing sequence in accordance with a selected anti-tachycardia pacing (ATP) protocol is delivered to the primary ATP ventricle at a selected coupling interval with respect to detection of a sense in the primary ATP ventricle, and further wherein the controller is programmed such that the secondary ATP ventricle is paced at a selected ATP offset interval with respect to the pace delivered to the primary ATP ventricle in the anti-tachycardia pacing sequence.

15. The device of claim 14 wherein the controller is further programmed to revert to a biventricular resynchronization pacing mode upon termination of the ventricular tachycardia.

16. The device of claim 15 wherein the controller is programmed such that the offset interval between paces to the ventricles gradually changes from the ATP offset interval to a programmed resynchronization offset interval upon termination of the ventricular tachycardia.

17. The device of claim 14 wherein the controller is programmed to select the primary ATP ventricle as the ventricle from which the earliest sense is detected during a cycle of the ventricular tachycardia.

18. The device of claim 14 wherein the controller is programmed to select the ATP offset interval to be approximately equal to a measured time delay between a sense in the primary ATP ventricle and a sense in the secondary ATP ventricle during a cycle of the ventricular tachycardia.

* * * * *

UNITED STATES PATENT AND TRADEMARK OFFICE
CERTIFICATE OF CORRECTION

PATENT NO. : 6,885,890 B2
DATED : April 26, 2005
INVENTOR(S) : Spinelli et al.

It is certified that error appears in the above-identified patent and that said Letters Patent is hereby corrected as shown below:

Column 9,
Line 5, delete "paging" and insert -- pacing --.
Line 64, after "to" delete ";" and insert -- : --.

Column 10,
Line 23, after "programmed" delete "t" and insert -- to --.
Line 24, insert -- a -- before "measured".

Signed and Sealed this

Sixth Day of June, 2006

JON W. DUDAS
*Director of the United States Patent and Trademark Office*